United States Patent [19]

Fahmy

[11] 4,284,626

[45] Aug. 18, 1981

[54] O-ARYL S-BRANCHED ALKYL ALKYLPHOSPHONODITHIOATE INSECTICIDES AND NEMATOCIDES

[75] Inventor: Mohamed A. Fahmy, Edison, N.J.

[73] Assignee: Mobil Oil Corporation, New York, N.Y.

[21] Appl. No.: 108,329

[22] Filed: Dec. 31, 1979

[51] Int. Cl.³ .................... A01N 57/022; C07F 9/40
[52] U.S. Cl. .................................. 424/222; 260/961
[58] Field of Search ........................ 260/961; 424/222

[56] References Cited

U.S. PATENT DOCUMENTS

| 3,642,960 | 2/1972 | Pitt et al. | 260/961 |
| 4,190,652 | 2/1980 | Hofer et al. | 260/961 |

Primary Examiner—Anton H. Sutto

Attorney, Agent, or Firm—C. A. Huggett; J. F. Powers, Jr.; E. J. Trojnar

[57] ABSTRACT

Compounds having the formula

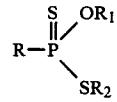

in which
   R is alkyl of 1 to 8 carbon atoms;
   $R_1$ is aryl;
   $R_2$ is branched alkyl of 3 to 8 carbon atoms; and their use as insecticides and nematocides, e.g., in controlling corn rootworm and southern armyworm.

22 Claims, No Drawings

O-ARYL S-BRANCHED ALKYL ALKYLPHOSPHONODITHIOATE INSECTICIDES AND NEMATOCIDES

CROSS-REFERENCE TO RELATED APPLICATIONS

An application entitled "BRANCHED-S-ALKYL PHOSPHONODITHIOIC HALIDE INTERMEDIATES AND PROCESS FOR THEIR PRODUCTION", Ser. No. 071,465, filed on Aug. 31, 1979 in the name of Mohamed A. Fahmy discloses certain intermediates useful for the production of insecticides and nematocides of this invention and the process for their preparation.

SUMMARY OF THE INVENTION

This invention relates to O-aryl S-branched alkyl alkylphosphonodithioate compounds and their use as insecticides and nematocides.

More particularly, the compounds of the invention have the formula

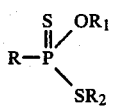

in which R is alkyl of 1 to 8 carbon atoms; $R_1$ is aryl; and $R_2$ is branched alkyl of 3 to 8 carbon atoms.

These compounds exhibit a wide range of insecticidal activity and are of particular interest in controlling corn rootworm and southern armyworm because of their stability and long residual activity.

DETAILED DESCRIPTION OF THE INVENTION

An important structural feature of the compounds of this invention is that $R_2$ in the above formula is branched alkyl. Certain O-arylphosphonodithioate insecticides are described in U.S. Pat. No. 3,209,020. However, none of the species described in the patent correspond to the above formula where $R_2$ is branched alkyl.

It has been found that the branched compounds of this invention possess high toxicity to southern armyworm. They also exhibit long residual activity to corn rootworm.

The compounds disclosed herein can be prepared by the method described in U.S. Pat. No. 3,209,020. Preferably, the compounds of this invention are prepared from a starting material which is a S-alkyl alkylphosphonodithioic halide, the preparation of which is illustrated in Example 1. A more detailed description of the preparation of these starting materials is contained in an application by M. Fahmy, Ser. No. 071,465, filed on Aug. 31, 1979, which application is incorporated herein by reference. The S-alkyl alkylphosphonodithioic halide is reacted with a phenol or substituted phenol in the presence of a base to arrive at the compounds of this invention.

The preferred reaction scheme is as follows:

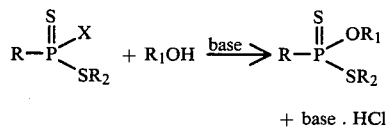

+ base . HCl in which

R is alkyl of 1 to 8 carbon atoms;
$R_1$ is aryl;
$R_2$ is branched alkyl of 3 to 8 carbon atoms; and
X is halogen, preferably Cl.

Suitable aryl groups include phenyl and phenyl mono-, di-, tri- or tetra-substituted with alkyl of 1 to 4 carbon atoms, alkoxy of 1 to 4 carbon atoms, alkylthio of 1 to 4 carbon atoms, alkylsulfinyl of 1 to 4 carbon atoms, or alkylsulfonyl of 1 to 4 carbon atoms, Cl, Br, F, nitro, or trifluoromethyl, or combinations of the foregoing.

The reaction is advantageously carried out at a temperature of about 20° C. to 100° C. in an organic solvent in the presence of a tertiary amine, water or aqueous base, such as aqueous NaOH.

Suitable organic solvents are, for example, benzene, toluene, cyclohexane, 2-butanone, and acetone.

Suitable tertiary amines include trimethyl amine, triethylamine, dimethyl aniline, diethyl aniline and pyridine.

The alkylphosphonodithioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 lbs/acre. Under ideal conditions, depending on the pest to be controlled, the lower rate may offer adequate protection. On the other hand, adverse weather conditions, resistence of the pest and other factors may require that the active ingredient be used in higher proportions.

When the pest is soil-borne, the formulation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting, after planting but before sprouting has taken place or after sprouting.

The following Examples illustrate the preparation of the compounds of this invention and their pesticidal properties. It will be understood that all of the compounds disclosed herein can be prepared by methods analogous to those described below.

EXAMPLE 1

Preparation of S-tert.-butyl ethylphosphonodithioic chloride (Intermediate)

To a solution of ethylphosphonothioic dichloride (80 g, 0.5 mol) in 500 ml dry toluene, was added 2-methyl-2-propanethiol (50 g, 0.55 mol). The solution was stirred while triethylamine (60 g, 0.6 mol) was added dropwise. After the complete addition of the amine, the mixture was stirred and heated up to 80° C. for three hours and allowed to stand overnight. The reaction mixture was washed with 5% cold HCl solution (100 ml) followed by another wash with 5% cold NaOH solution (100 ml), finally washed twice with water (100 ml each), and dried over magnesium sulfate. Toluene was evaporated under a water aspirator vacuum, and the oil residue was distilled. The product distilled at 78°–80° C./0.2 mm. The yield was 60 g (55.4% of theoretical yield). The structure was confirmed by NMR.

EXAMPLE 2

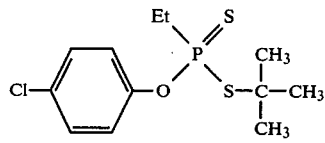

To a solution of S-tert.-butyl ethylphosphonodithioic chloride (10 g, 0.046 mol) in 15 ml acetone was added 4-chloro-phenol (6.5 g, 0.05 mol), followed by triethylamine (6.0 g, 0.06 mol). The mixture was stirred at room temperature overnight, then heated to 50° C. for one hour. The solution was diluted with toluene, filtered from the amine hydrochloride salt, extracted with water, 5% NaOH solution, then water again. The organic phase was dried over anhydrous $Na_2SO_4$ and the solvent was stripped off under vacuum. The residual liquid was subjected to high vacuum (0.05 mm) for one hour at 90°–100° C., to evaporate any unreacted phosphonodithioic chloride. The resulting clear liquid weighing 13.5 g (87.7% yield) is a pure product of the title structure as confirmed by NMR.

EXAMPLES 3–21

In a manner analogous to that of Example 2 the following compounds were prepared.

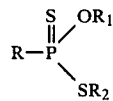

TABLE 1

| EXAMPLE | R | $R_1$ | $R_2$ |
|---|---|---|---|
| 3 | $CH_3$ | phenyl | tert.-butyl |

TABLE 1-continued

| EXAMPLE | R | $R_1$ | $R_2$ |
|---|---|---|---|
| 4 | $C_2H_5$ | phenyl | tert.-butyl |
| 5 | $C_2H_5$ | phenyl | sec.-butyl |
| 6 | $CH_3$ | 2-methylphenyl | tert.-butyl |
| 7 | $C_2H_5$ | 2-methylphenyl | sec.-butyl |
| 8 | $C_2H_5$ | 2-methylphenyl | tert.-butyl |
| 9 | $CH_3$ | 4-methylphenyl | tert.-butyl |
| 10 | $C_2H_5$ | 4-methylphenyl | tert.-butyl |
| 11 | $CH_3$ | 4(methylthio)phenyl | tert.-butyl |
| 12 | $Ch_2H_5$ | 4(methylthio)phenyl | tert.-butyl |
| 13 | $C_2H_5$ | 3-methyl-4-(methylthio)phenyl | tert.-butyl |
| 14 | $CH_3$ | 4-chlorophenyl | tert.-butyl |
| 15 | $C_2H_5$ | 4-chlorophenyl | sec.-butyl |
| 16 | $C_2H_5$ | 4-fluorophenyl | tert.-butyl |
| 17 | $C_2H_5$ | 2-fluorophenyl | tert.-butyl |
| 18 | $C_2H_5$ | 2-methyl-4-chlorophenyl | tert.-butyl |
| 19 | $C_2H_5$ | 2-methyl-4-chlorophenyl | sec.-butyl |
| 20 | $C_2H_5$ | 4-nitrophenyl | tert.-butyl |
| 21 | $C_2H_5$ | 4-nitrophenyl | sec.-butyl |

EXAMPLE 22

Testing for corn rootworm intrinsic activity and activity against Southern Armyworm.

A. Corn rootworm intrinsic activity (CRW)

The test compound is prepared in a one percent solution with acetone or ethanol. The stock solution is then diluted with an aqueous solution of Tween 20 and water to the appropriate concentration (i.e., 100, 10, 1, 01, 0.01 ppm). Two ml of this solution is pipetted into a 9 cm. petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in TABLE 2.

B. Southern Armyworm intrinsic activity (SAW)

Stock solution (1%) of test material was made in acetone and diluted to the desired concentration by a 500 ppm Tween 20 aqueous solution. Lima bean leaves are dipped into the solution and transferred to petri dishes (100×15 mm) containing two filter papers moistened with 2 ml water. Each petri dish contained one leaf and was kept open to dry out the solution on the leaf. Five third instar larvae of Southern Armyworm (*Spodoptera eridania*) were added to the leaf and the dish was finally covered.

The insects were held at 78° F. for 72 hours and percent kill was recorded. The results are an average of two replicas and are reported in TABLE 2.

TABLE 2

| Compound of Example | % Control | | | | |
|---|---|---|---|---|---|
| | SAW | | | CRW | |
| | 500 | 100 | Rate (ppm) | 1 | 0.1 |
| 2 | 100 | 100 | | — | — |
| 3 | 100 | 100 | | 100 | 70 |
| 4 | 100 | 65 | | 95 | 50 |
| 6 | 90 | 75 | | 100 | |
| 7 | 90 | 0 | | — | — |
| 8 | 90 | 40 | | 100 | — |
| 14 | 100 | 95 | | 70 | 30 |
| 15 | 100 | 85 | | — | — |
| 16 | 100 | 100 | | — | — |
| 17 | 100 | 100 | | — | — |
| 18 | 100 | 95 | | — | — |
| 19 | 100 | 25 | | — | — |
| 20 | 100 | 90 | | — | — |
| 21 | 90 | — | | | |

I claim:

1. A method for controlling insects and nematodes which comprises applying thereto or their habitat a pesticidal amount of a compound of the formula

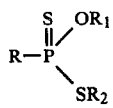

in which
R is an alkyl of 1 to 8 carbon atoms;
$R_1$ is phenyl or phenyl substituted with 1 to 4 members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro and trifluoromethyl; and
$R_2$ is a tertiary alkyl of 4 to 8 carbon atoms.

2. A method for controlling corn rootworm which comprises providing a pesticidal amount in the soil of a compound of the formula

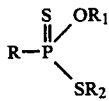

in which
R is an alkyl of 1 to 8 carbon atoms; and
$R_1$ is phenyl or phenyl substituted with 1 to 4 members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro and trifluoromethyl; and
$R_2$ is a tertiary alkyl of 4 to 8 carbon atoms.

3. The method of claim 2 in which $R_1$ is phenyl.
4. The method of claim 2 in which R is methyl or ethyl.
5. The method of claim 2 in which R is methyl or ethyl; and $R_2$ is t-butyl.
6. The method of claim 2 in which
R is ethyl;
$R_1$ is phenyl; and
$R_2$ is t-butyl.
7. The method of claim 2 in which
R is ethyl;
$R_1$ is methyl-phenyl; and
$R_2$ is t-butyl.
8. The method of claim 2 in which
R is methyl;
$R_1$ is methyl-phenyl; and
$R_2$ is t-butyl.
9. The method of claim 2 in which
R is methyl;
$R_1$ is chlorophenyl; and
$R_2$ is t-butyl.
10. The method of claim 2 in which
R is ethyl;
$R_1$ is chlorophenyl; and
$R_2$ is t-butyl.
11. The method of claim 2 in which R is methyl or ethyl; and $R_1$ is phenyl.

12. A compound of the formula

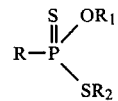

in which
R is an alkyl of 1 to 8 carbon atoms;
$R_1$ is phenyl or phenyl substituted with 1 to 4 members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro and trifluoromethyl; and
$R_2$ is a tertiary alkyl of 4 to 8 carbon atoms.

13. A compound of claim 12 in which $R_1$ is phenyl.
14. A compound of claim 12 in which $R_2$ is t-butyl.
15. A compound of claim 12 in which R is methyl or ethyl.
16. A compound of claim 12 in which R is methyl or ethyl; and
$R_1$ is phenyl.
17. A compound of claim 12 in which
R is ethyl;
$R_1$ is phenyl; and
$R_2$ is t-butyl.
18. A compound of claim 12 in which
R is ethyl;
$R_1$ is methyl-phenyl; and
$R_2$ is t-butyl.
19. A compound of claim 12 in which
R is methyl;
$R_1$ is methyl-phenyl; and
$R_2$ is t-butyl.
20. A compound of claim 12 in which
R is methyl;
$R_1$ is chlorophenyl; and
$R_2$ is t-butyl.
21. A compound of claim 12 in which
R is ethyl;
$R_1$ is chlorophenyl; and
$R_2$ is t-butyl.
22. A composition comprising, as the active ingredient, a compound of the formula

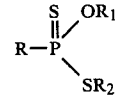

in which
R is an alkyl of 1 to 8 carbon atoms;
$R_1$ is phenyl or phenyl substituted with 1 to 4 members selected from the group consisting of alkyl of 1 to 4 carbon atoms, alkoxy of 1 to 4 carbon atoms, alkythio of 1 to 4 carbon atoms, alkylsulfinyl of 1 to 4 carbon atoms, alkylsulfonyl of 1 to 4 carbon atoms, Cl, Br, F, nitro and trifluoromethyl; and
$R_2$ is a tertiary alkyl of 4 to 8 carbon atoms; in an amount effective as an insecticide or a nematocide, and an inert, non-phytotoxic organic solvent or solid carrier.

* * * * *

UNITED STATES PATENT AND TRADEMARK OFFICE
CERTIFICATE OF CORRECTION

PATENT NO. : 4,284,626
DATED : August 18, 1981
INVENTOR(S) : Mohamed A. Fahmy

It is certified that error appears in the above—identified patent and that said Letters Patent is hereby corrected as shown below:

Column 4, line 11, Example 12 of Table 1, correct "$Ch_2H_5$" to read -- $C_2H_5$ --.

Signed and Sealed this

Twenty-third Day of August 1983

[SEAL]

Attest:

GERALD J. MOSSINGHOFF

Attesting Officer     Commissioner of Patents and Trademarks